United States Patent

Soós et al.

Patent Number: 4,999,454
Date of Patent: Mar. 12, 1991

[54] PROCESS FOR THE PREPARATION OF TRICHLOROMETHYL CARBINOLS

[75] Inventors: Rudolf Soós; József Nemes; Miklós Szelestei; István Schler; László Vidra, all of Budapest; István Székely, Dunakeszi, all of Hungary

[73] Assignee: Chinoin Gyogyszer ES Vegyeszeti Termekek Gyara RT., Budapest, Hungary

[21] Appl. No.: 784,692

[22] Filed: Oct. 3, 1985

Related U.S. Application Data

[63] Continuation of Ser. No. 559,799, Dec. 9, 1983, abandoned.

[30] Foreign Application Priority Data

Dec. 13, 1982 [HU] Hungary ............... 4005/82

[51] Int. Cl.[5] .................. C07C 67/08; C07C 69/007; C07C 69/145; C07C 33/42
[52] U.S. Cl. ................... 560/213; 560/106; 560/111; 560/262; 568/700; 568/821; 568/826; 568/828; 568/838; 568/839; 568/845
[58] Field of Search ............. 560/262, 238, 106, 111, 560/231; 568/845, 821, 826, 828, 838, 839, 700

[56] References Cited

U.S. PATENT DOCUMENTS 3,124,599  3/1964  Guest et al. .................. 560/240
4,190,730  2/1980  Mori et al. .................... 568/845

OTHER PUBLICATIONS

Migrdichian, Organic Synthesis, vol. 1, Reinhold Publishing Corporation, N.Y. 1957, p. 323.

Primary Examiner—Vivian Garner
Attorney, Agent, or Firm—Herbert Dubno; Jonathan Myers

[57] ABSTRACT

The invention is directed to a new process for the preparation of carbinols of the general formula I

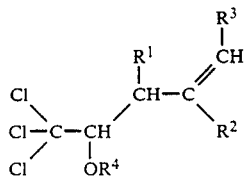

by reaction chloral and olefins of the general formula

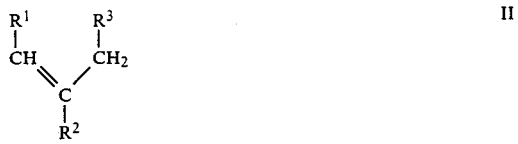

and by optional acylation of the product comprising dissolving a catalyst of the general formula III

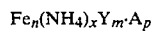

in chloral, then adding the olefin of the general formula II in order to produce a complex of the general formula IV

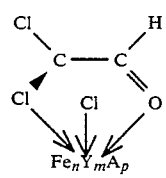

from which a complex of the general formula V

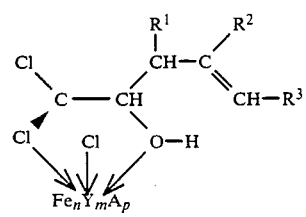

is formed, and from the reaction mixture a compound of the general formula I is obtained whereafter
(a) the residual complex of the general formula V dissolved in the product is decomposed with an acidic solution and if desired the obtained product is distilled or
(b) the product in the reaction mixture is acylated.

The compounds prepared according to the invention can be utilized as intermediates when preparing e.g., permethrin and other pyrethroid insecticides.

8 Claims, No Drawings

PROCESS FOR THE PREPARATION OF TRICHLOROMETHYL CARBINOLS

This is a continuation of co-pending application Ser. No. 559,799 filed on Dec. 9, 1983, now abandoned.

The present invention relates to a process for the preparation of trichloromethyl carbinols.

The substituents throughout the specification are defined as follows:

R stands for alkyl containing 1 to 4 carbon atoms, $R^1$, $R^2$ and $R^3$ stand for hydrogen or alkyl containing 1 to 4 carbon atoms or $R^1$ and $R^2$ or $R^1$ and $R^3$ together form an alkylene group, $R^4$ stands for alkanoyl having 1 to 4 carbon atoms or aroyl or hydrogen, Y stands for halide, sulphate, phosphate, oxalate or acetate, A represents $H_2O$, $ROH$, $R_3N$, n represents 1 to 3, m stands for 1 to 3, p stands for 1 to 6, x represents 0 or 1.

The invention is directed to a new process for the preparation of carbinols of the formula I

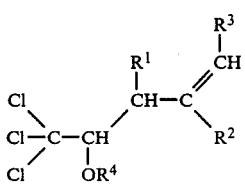

by reacting chloral and olefins of the formula II

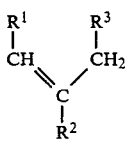

and by optional acylation of the product comprising dissolving a catalyst of the formula III $$Fe_n(NH_4)_x Y_m \cdot A_p \qquad III$$

in chloral, then adding the olefin of the formula II in order to produce a complex of the formula IV

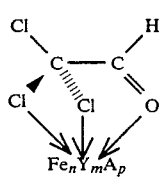

from which a complex of the formula V

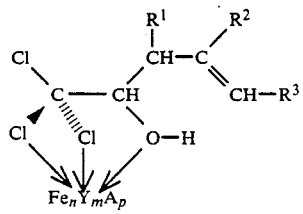

is formed, and from the reaction mixture a compound of the formula I is obtained, whereafter (a) the residual complex of the formula V dissolved in the product is decomposed with an acidic solution and if desired the obtained product is distilled or (b) the product in the reaction mixture is acylated.

The compounds prepared according to the invention can be utilized as intermediates when preparing e.g. permethrin and other pyrethroid insecticides (Collect. Czeh. Commun. 1959, 24, 2230).

The reaction of chloral and olefins catalyzed by aluminum chloride is known for the preparation of unsaturated trichloromethyl carbinols (Bull. Chim. Soc. France, 1956, 204–208). In this reaction when using e.g. isobutene and chloral reactants, a mixture of 1,1,1-trichloro-2-hydroxy-4-methyl-4-pentene and 1,1,1-trichloro-2-hydroxy-4-methyl-3-pentene is formed. Authors explained the formation of isomers as follows: after complex formation the aluminium chloride catalyst forms from chloral a "trichloromethyl oxocarbenium" reactive intermediate, which results in the formation of "3-pentene" isomer. The reaction of chloral and olefin is also catalyzed by the hydrochloric acid which is present in the mixture. In this case the carbon-carbon double bond is formed by the reactive intermediate "trichloromethyl hydroxy carbenium ion", which is subjected to addition according to the Prins mechanism and after losing a proton the "4-pentene" isomer is obtained. The aluminum chloride catalyzed reaction has several drawbacks, particularly in industry. The main disadvantage is the formation of the isomer mixture, but the ratio of the isomers is not constant either. The "3-ene" and "4-ene" isomers cannot be prepared in pure form by isomerisation either. In U.S. Pat. No. 4,117,247 the preparation of pure "3-ene" isomer by isomerization catalyzed by strong inorganic or organic acid or transition metals belonging to groups 6B, 7B and 8 or compounds thereof is disclosed, but we observed that the pure "3-ene" can be obtained only after crystallization of the "3-ene" isomer. Although the "3-ene" isomer can be enriched in a ratio of 4:1, but the isomerization leads to an equilibrium, and in addition to that during isomerization with acid a strong tar formation occurs. The water sensitivity of the aluminum chloride catalyst means a further problem. Water present in chloral reacts with aluminum chloride under hydrochloric acid evolution and thus the actual amount of the catalyst is uncertain. It often occurs that the reaction takes place only partially, which is dangerous since a significant amount of isobutene may be released when processing the reaction mixture.

The aluminum chloride is unfavorable also from the point of view of the removal of the catalyst. When the reaction is terminated the aluminum chloride catalyst has to be removed by washing with water. Apart from the aluminum trichloride catalyst in U.S. Pat. No. 4,117,247 as catalysts generally Lewis acids, inorganic acids and organic acids are disclosed for the reaction of isobutene and chloral.

We examined the catalytic behavior of ferric chloride among the Lewis acids during the reaction of isobutene and chloral. We observed, however, that in the reaction of isobutene and chloral said catalyst catalyzed the formation of another compound and not that of the compound of the formula I. A product was isolated with 65% yield, (m.p.: 112°–114° C., Rf=0.55 in normal hexane) physical chemical properties of which were quite different from the properties of 1,1,1-trichloro-4-methyl-4-pentene-2-ol (oil, Rf=0.37 in benzene).

We have found, that if in the reaction ferric chloride-triethyl amine basic catalyst or iron complexes, such as iron ammonium sulphate, ferric chloride-hexahydrate etc. are used, then 1,1,1-trichloro-4-methyl-4-pentene-2-ol corresponding to the formula I was obtained substantially with a quantitative yield. We have found, that the ideal catalysts for the reactions are not the compounds of Lewis acid type, i.e. not compounds which are electron acceptors having empty orbit, but basic, neutral or acidic ferric or ferrous complexes or salts (possessing ligand properties).

We presume that during the reaction a complex is formed from chloral and ferric chloride hexahydrate, in which the carbonyl group of chloral is activated for an "ene-type" addition and thus the product is formed through complexes of the formulae IV and V.

In the case of the iron complexes—unlike the aluminum chloride—a reactive intermediate complex is formed, which activates the II-electron system of the carbonyl bond partly by increasing the electron negativity of the oxygen due to the binding to the iron center of the ferric chloride as a ligand and partly by causing an electron suction of opposite direction due to the orientation of one or two chlorine atoms of the —CCl$_3$ group towards the iron center.

Our conclusions concerning the mechanism is supported by the reaction of opposite direction upon the effect of the catalyst. We have found, that 1,1,1-trichloro-4-methyl-4-pentene-2-ol is decomposed in the presence of 5% catalyst at 80°–90° C. at reduced pressure, 15 Hgmm upon heating and chloral is formed. The reaction can also be explained by the coordination complex of iron(III)center of the formula II, decomposing to isobutene and chloral complex according to a "retro-ene" mechanism.

The detected chloral is released by the shift of the complex equilibrium upon distillation.

According to a simple embodiment of the present invention the iron(III)catalyst, e.g. ferric chloride hexahydrate is dissolved in chloral the solution is then cooled to −20° to +10° C. and olefin is introduced to the reaction mixture at a rate so that the temperature does not exceed 15° C.

The addition reaction of chloral is an exothermic reaction but it can be ambiguously controlled by the addition of olefin in portions. One of the advantages of the process according to the invention is that the catalyst is not water sensitive; on the contrary a catalyst containing crystal water can be used. (In the case of aluminum chloride in the presence of water not only the catalyst activity ceases when the catalyst is decomposed, but the formed hydrochloric acid catalyzes the polymerization of the chloral, and in extreme case this can lead to the entire set of the reaction mixture).

A further significance of the employment of neutral and mainly basic iron complexes is elimination of the polymerization of chloral. Chloral is polymerized upon proton or Lewis acid catalyst. No polymerization occurs when using basic or neutral complex iron catalyst.

As to the reaction time the quality of the olefin is important. The terminal olefins react most quickly and in this case the reaction is substantially terminated when introducing the olefin.

The processing of the obtained reaction mixture is a further important feature of the process of the invention.

At the end of the reaction the catalyst has to be removed because of the reversibility in the presence of the complex iron catalysts. A simple method is to use a wash with acid, e.g. with hydrochloric acid. When washing with hydrochloric acid the reaction mixture is easily partitioned to product layer and aqueous layer and after separation only the water remained dissolved in the product has to be removed, preferably by heating at reduced pressure.

The acidic decomposition can be easily performed, but its use means a loss, as the washing of the product with aqueous hydrochloric acid solution can take away 5% of the product. The complete termination of the water removal can be hardly detected.

The reversible activity of the catalyst can also be eliminated by the preparation of ester derivatives.

To the thus obtained reaction mixture e.g. an acyl anhydride can be added and so in the reaction of isobutene and chloral (iron-complex catalyst) directly 1,1,1-trichloro-2-acyloxy-4-methyl-4-pentene can be obtained, which can be directly used in further reactions or can be isolated after extraction in a pure state.

In this case esterification takes place, but neither a conventional proton catalysis (e.g. use of concentrated sulphuric acid) nor any acid binding agent (such as concentrated sulphuric acid) are needed as the complex contains a suitably activated hydroxyl for the esterification reaction.

After esterification the reaction mixture can be directly used for the further reaction steps, but if necessary it can be processed by extraction (aqueous washing) with a good yield and can be isolated in pure state, as the acylated product is substantially insoluble in water.

Further details of the invention can be found in the Examples.

EXAMPLE 1

To 97.5 ml. (1 mole) of anhydrous chloral 0.5 g. of ferric chloride hexahydrate is added. To the obtained yellow clear solution 58–59 g. of isobutylene are introduced so that the temperature does not exceed 15°–20° C. To the reaction mixture a mixture of 35 ml. of water and 15 ml. of concentrated hydrochloric acid is added and the layers are separated. The organic layer is washed with water, diluted with benzene and water is removed from the mixture in a vacuo of 100 Hgmm. 194.6 g. (96.5%) of 1,1,1-trichloro-4-methyl-4-pentene-2-ol are obtained. Active ingredient content: 98.2%. The product can be further purified by vacuum distillation.

Analysis: $^1$H-NMR (CDCl$_3$): 4.97 (broad s, 1H, C$\underline{H}$O), 4.08–4.4 (dq, 2H, =CH$_2$), 2.25–3.0 (m, 2H, C$\underline{H}_2$CHOCH), 1.93—(s, 3H, C$\underline{H}_3$).

thin layer chromatography: $R_f$=0.37 (benzene)

Silicagel G plate is developed with phosphoro moybdenic acid reactant.

Gaschromatography: OV-225 (15), 120° C.−10° C./min: 225.2 sec.

EXAMPLE 2

One may proceed as disclosed in Example 1 but as catalyst 0.5 g. of ferrous sulphate-dihydrate is added to the reaction mixture. 189.5 g. (94%) of 1,1,1-trichloro-4-methyl-4-pentene-2-ol are obtained. The analytical results are the same as given in Example 1.

EXAMPLE 3

In 3.9 ml. (0.04M) of chloral 0.1 g. of ferric chloride-hexahydrate is dissolved, and then 3.95 ml. (0.04M) of cyclohexene are added dropwise at 10°–25° C. After stirring for 2 hours 20 ml. of water and 4 ml. of concentrated hydrochloric acid are added. The layers are separated and the aqueous layer is extracted with carbon tetrachloride. The organic layers are combined, dried, filtered and the solvent is distilled off at reduced pressure. 7.6 g. (82.8%) of trichloromethyl-(2-cyclohexenyl-1-yl)-carbinol are obtained.

Analysis: thin layer chromatography: $R_f=0.71$ (benzene)

The silicagel plate is developed with phosphoro molybdenic acid reactant.

EXAMPLE 4

One may proceed as given in Example 1 but hydrochloric acid used to decompose the reaction mixture is replaced with 124 ml. (1.3M) of acetic acid anhydride which is added within 1 hour below 35° C. so that after adding the first 10 ml. 3 drops of concentrated sulphuric acid are added to the reaction mixture. The mixture is then taken up in 200 ml. of dichloroethane, washed with 40 ml. of water and 15 ml. of concentrated hydrochloric acid, whereafter the mixture is washed with water, dried, filtered and the organic solvent is distilled off at reduced pressure. 270 g. of crude product are obtained, which are purified by fractionated distillation. As a main cut a cut distilling at 94°–98° C. at 10 Hgmm. is collected. Yield: 228.2 g. (93%) of 1,1,1-trichloro-4-methyl-2-acetoxy-4-pentene.

Analytical data:
Thin layer chromatography: $R_f=0.88$ (benzene)
$^1$H-NMR (CHCl$_3$,): 2.2 (s, 3H, C$\underline{H}_3$CO), 4.87 (broad s, 2H, =C$\underline{H}_2$), 5.7 (dd, 1H, C$\underline{H}$OAc).

EXAMPLE 5

Reaction of chloral and i-butene under strictly anhydrous conditions in the presence of anhydrous ferric chloride catalyst:

(comparative test)

To a mixture of 78.5 g. (48.5 cm$^3$) (0.5 mole) chloral and 0.5 g. of anhydrous ferric chloride 29 g. (0.5 mole) of iso-butene are bubbled at 40° C. whereafter 200 cm$^3$ of ether are added to the reaction mixture. After filtration the ethereal layer is dried above anhydrous sodium sulphate and the solvent is distilled off. To the obtained thick oil 3 cm$^3$ n-hexane are added and the thus obtained crystalline substance is filtered off. The product is washed with 2×20 cm$^3$ of n-hexane and dried at room temperature.

Yield: 57.0 g. Yield: 65%.

The obtained substance is recrystallized from a 10:1 mixture of n-hexane and ether. Yield: 50.8 g. (58%).

Thin layer chromatogram of the product in n-hexane: developing agent: a 20% ethanolic solution of phosphoro molybdenic acid
$R_f=0.55$
$^1$H-NMR: 5.06 singlet, 4.325 doublet, 1.99 doublet, 1.425 singlet
Ms: 350.9, m.p.: 112°–114° C.

One may proceed as disclosed in Example 1 but as catalysts one can use catalysts given in the Table below:

| Example | molar ratio of chloral/i-butene | used catalyst | amount of catalyst % | yield % |
|---|---|---|---|---|
| 6 | 1/1 | Fe(NH$_4$)$_2$(SO$_4$)$_2$ × 6H$_2$O | 5.0 | 93–94 |
| 7 | 1/1 | anhydrous FeCl$_2$ - triethylamine 1 mol./1 mol. | 5.0 | 45–46 |
| 8 | 1/1 | anhydrous FeCl$_3$ - triethylamine 1 mol./2 mol. | 5.0 | 80–82 |
| 9 | 1/1 | FeSO$_4$ × 2H$_2$O | 5.0 | 78 |
| 10 | 1/1 | Fe$_3$(PO$_4$)$_2$ × 8H$_2$O | 5.0 | 74–75 |
| 11 | 1/1 | FeBr$_3$ × 6H$_2$O | 5.0 | 94–95 |
| 12 | 1/1 | (NH$_4$)$_3$[Fe(C$_2$O$_4$)$_3$] × 3H$_2$O | 5.0 | 92–93 |

Analytical data of the product correspond to the data given in Example 1.

We claim:
1. A process for the preparation of a compound of the formula (I)

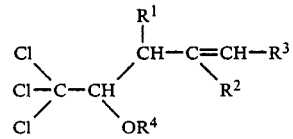

wherein
R$^1$, R$^2$ and R$^3$ each is hydrogen or alkyl containing 1 to 4 carbon atoms, or R$^1$ and R$^2$ together or R$^1$ and R$^3$ together form alkylene; and R$^4$ is hydrogen, C$_1$-C$_4$ alkanoyl, or aroyl, which comprises the step of reacting a compound of the formula (II)

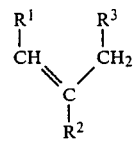

with chloral in a 1 to 1 molar ratio in the presence of a catalyst selected from the group consisting of FeCl$_3$ × 6H$_2$O, FeSO$_4$ × 2H$_2$O, Fe(NH$_4$)$_2$(SO$_4$)$_2$ × 6H$_2$O, anhydrous FeCl$_3$ and triethylamine in a 1 to 2 molar ratio, Fe$_3$(PO$_4$)$_2$ × 8H$_2$O, FeBr$_3$ × 6H$_2$O and (NH$_4$)$_3$ Fe(C$_2$O$_4$)$_3$ × 3H$_2$O to yield a reaction product;
and in the case where the desired compound is the compound of the formula (I) where R$^4$ is hydrogen, decomposing the reaction product with an acid to partition the reaction product into an organic layer containing the desired product and an aqueous layer containing the catalyst, and separating the organic layer from the aqueous layer; and in the case where the desired compound is the compound of the formula (I) where $R^4$ is $C_1$-$C_4$ alkanoyl or aroyl, acylating the reaction product with an acylating agent to yield the compound of the formula (I) where $R^4$ is $C_1$-$C_4$ alkanoyl or aroyl, and isolating the compound of the formula (I).

2. The process defined in claim 1 wherein the catalyst is selected from the group which consists of $FeCl_3 \times 6H_2O$, $FeSO_4 \times 2H_2O$ and $Fe(NH_4)_2(SO_4)_2 \times 6H_2O$.

3. The process defined in claim 1 in the case where the desired compound is the compound of the formula (I) wherein $R^4$ is hydrogen wherein the separated organic layer containing the compound of the formula (I) is purified by distillation.

4. The process defined in claim 1 in the case where the desired compound is the compound of the formula (I) wherein $R^4$ is $C_1$-$C_4$ alkanoyl or aroyl wherein the acylating agent is an acid anhydride or acid chloride.

5. The process defined in claim 4 wherein the acid anhydride is acetic anhydride, in the presence of concentrated sulfuric acid.

6. The process defined in claim 1 in the case where the desired compound is the compound of the formula (I) wherein $R^4$ is hydrogen wherein a mixture of hydrochloric acid and water is used to decompose the reaction product.

7. The process defined in claim 1 wherein the compound of the formula (II) is isobutylene.

8. The process defined in claim 1 wherein the catalyst is used at a concentration of 0.001 to 7.5% by weight calculated with respect to the chloral starting material.

* * * * *